United States Patent [19]

Noguchi et al.

[11] 4,029,813
[45] June 14, 1977

[54] FUNGICIDAL COMPOSITIONS CONTAINING BISTHIOUREIDO-BENZENES AND METHODS FOR USE THEREOF

[75] Inventors: Teruhisa Noguchi, Tokyo; Keisuke Kohmoto, Tottori; Kimpei Kato, Ohiso, all of Japan

[73] Assignee: Nippon Soda Company Limited, Tokyo, Japan

[22] Filed: Nov. 3, 1975

[21] Appl. No.: 628,574

Related U.S. Application Data

[63] Continuation-in-part of Ser. No. 128,148, March 25, 1971, abandoned, which is a continuation-in-part of Ser. No. 771,269, Oct. 28, 1968, abandoned.

[30] Foreign Application Priority Data

| Oct. 30, 1967 | Japan | 42-69358 |
| Dec. 27, 1967 | Japan | 42-83245 |
| Apr. 13, 1968 | Japan | 43-24528 |
| Apr. 19, 1968 | Japan | 43-25829 |
| June 18, 1968 | Japan | 43-41587 |
| June 18, 1968 | Japan | 43-41589 |

[52] U.S. Cl. .............................. 424/300; 260/470; 424/301
[51] Int. Cl.² ........................................ A01N 9/12
[58] Field of Search ................... 424/300; 260/470

[56] References Cited

UNITED STATES PATENTS

| 3,242,208 | 3/1966 | Martin | 260/552 |
| 3,745,187 | 7/1973 | Noguchi et al. | 424/300 |

*Primary Examiner*—Leonard Schenkman
*Attorney, Agent, or Firm*—Gordon S. Rogers

[57] ABSTRACT

Fungicidal compositions are provided containing as the active constituent compounds having the formula:

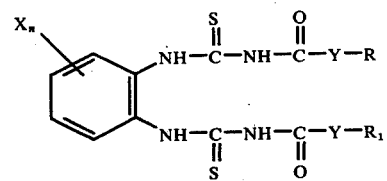

wherein each of R and $R_1$ represents a member of the group consisting of alkyl containing from 1 to 12 carbon atoms, alkyl containing from 1 to 2 carbon atoms substituted with halogen, methoxy or phenyl, alkenyl containing 2 to 3 carbon atoms, alkynyl containing 2 to 3 carbon atoms, aryl containing not more than 10 carbon atoms, aryl containing not more than 10 carbon atoms substituted with halogen or methyl; each X represents halogen, nitro or methyl; n represents an integer from 0 to 3; and Y represents oxygen or sulfur, with the proviso that when Y represents sulfur, each R and $R_1$ represents alkyl containing 1 to 12 carbon atoms.

These compounds may be prepared in accordance with the following equation:

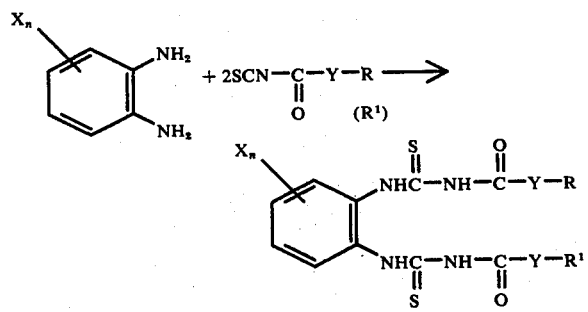

wherein R, $R^1$, X, Y and n are as stated above. These compounds have broad fungicidal activity with very low mammalian toxicity.

16 Claims, No Drawings

FUNGICIDAL COMPOSITIONS CONTAINING BISTHIOUREIDO-BENZENES AND METHODS FOR USE THEREOF

This application is a continuation-in-part of U.S. patent applicaion Ser. No. 128,148, filed Mar. 25, 1971, which in turn is a continuation-in-part of U.S. patent application Ser. No. 771,269, filed Oct. 28, 1968, both now abandoned.

This invention relates to novel bis-thioureido-benzenes having superior fungicidal activity and particularly to fungicidal compositions containing one or more of said novel compounds, and further includes methods for combatting fungi with the said compositions.

The novel compounds used in the compositions and processes of the present invention are characterized by the following formula:

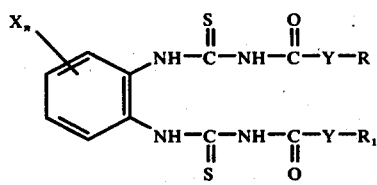

wherein each of R and $R_1$ represents a member of the group consisting of alkyl containing from 1 to 12 carbon atoms, alkyl containing from 1 to 2 carbon atoms substituted with halogen, methoxy or phenyl, alkenyl containing 2 to 3 carbon atoms, alkynyl containing 2 to 3 carbon atoms, aryl containing not more than 10 carbon atoms, aryl containing not more than 10 carbon atoms substituted with halogen or methyl; each X represents halogen, nitro or methyl; $n$ represents an integer from 0 to 3; and Y represents oxygen or sulfur, with the proviso that when Y represents sulfur, each R and $R^1$ represents alkyl containing 1 to 12 carbon atoms.

The compounds have superior fungicidal activity against various plant diseases such as rice blast disease, cucumber anthracnose, cercospora leaf spot of sugar beets and rice sheath bligh disease. It is an advantage of the invention that said compounds have very low mammalian toxicity.

The compounds of this invention can be prepared by the reaction illustrated below, wherein R, $R^1$, X, Y and $n$ are defined as above;

Equation 1

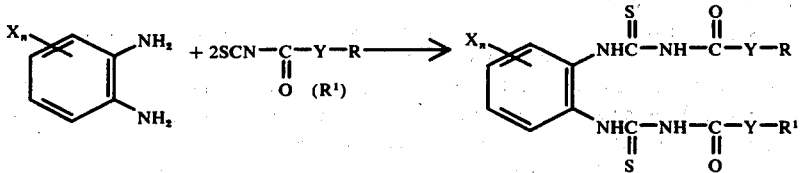

The reaction equation (1) is carried out in an inert organic solvent such as acetone, methylethylketone, methanol, ethanol, dioxane, acetonitrile, benzene or toluene, at a temperature of 0°–150° C., preferably 10°–60° C., ordinarily in about 10 minutes to 1 hour, but occasionally in several hours. After the reaction ends, the compound is isolated from the reaction mixture by conventional techniques. For example, the reaction mixture may be cooled or added to water. The precipitated material is separated from the solution by filtration. Instead, solvent may be distilled off from the reaction mixture. If necessary, the prepared compound may be further purified by washing with water and by washing with water and by recrystallizing from a solvent such as acetone, methanol, ethanol and dioxane.

In order to facilitate a clear understanding ot the invention, the following preferred specific embodiments are described as illustrative and not as limiting the invention.

EXAMPLE 1

1,2-Bis [(3-ethoxycarbonyl) thioureido] benzene (Compound 2)

59.0 g. (0.54 mol.) of ethyl chloroformate were added to 54.4 g. (0.56 mol.) of potassium thiocyanate in 300 ml. of acetone at room temperature under agitation, and the mixture was heated and kept at a room temperature of 35°–45° C. on a water bath for 1 hour. Then the mixture containing the resulting ethoxycarbonylisothiocyanate was cooled and kept at a temperature of 10°–20° C. on an ice water bath under agitation. 15.5 g. (0.143 mol.) of o-phenylenediamine were dropped into the mixture, while it was maintained at a temperature of 10°–20° C. on an ice water bath under agitation. Then the reaction mixture was kept at room temperature for 1 hour, and allowed to stand to precipitate a large quantity of crystals. The reaction mixture was filtered, and the recovered crystals were washed with water and dried.

47 g. of crystals were obtained. The crystals were light yellow, and had a decomposition point of 190°–191° C. Colorless plates having the decomposition point of 194° C. were obtained by recrystallization from acetone.

EXAMPLE 2

4-nitro-1,2-Bis [(3-ethoxycarbonyl) thioureido] benzene (Compound 7)

19.0 g. (0.175 mol.) of ethyl chloroformate were added to 18.0 g. (0.185 mol) of potassium thiocyanate in 150 ml. of acetonitrile at room temperature under agitation, and the mixture was heated and kept at a temperature of 35°–45° C. on a water bath. 12.3 g. (0.08 mol. ) of 4-nitro-o-phenylenediamine were dropped into the mixture containing the resulting ethoxycarbonylisothiocyanate, while it was maintained at a temperature of 20°–30° C. The reaction mixture was heated on a steam bath for one hour under reflux. Then the reaction mixture was cooled and about 500 ml. of cold water was added thereto.

33.0 g. of crystals were obtained following the procedure of Example 1. Light yellow needles having the decomposition point of 205°–206° C. were obtained by recrystallization from acetone.

EXAMPLE 3

1,2-Bis [3-(β-Methoxy)-ethoxycarbonyl] thioureido benzene (Compound 11)

13.8 g. (0.1 mol.) of 2-methoxyethylchloroformate were added to 10.8 g. (0.11 mol.) of potassium thiocyanate in 80 ml. of acetone at room temperature under agitation, and the mixture was heated and kept at a temperature of 40°–45° C. for 1 hour on a water bath. 4.0 (0.037 mol.) of o-phenylenediamine were dropped into the mixture containing the 2-(methoxy)-ethoxycarbonylisothiocyanate produced from said reactants while the mixture was maintained at a temperature of 10°–20° C. on an ice water bath. The reaction mixture was heated on a steam bath for 1 hour under reflux. Then the reaction mixture was cooled to room temperature and about 300 ml. of water was added to the cooled mixture.

14.0 g. of the crystals which formed were recrystalized from acetone to obtain colorless needles having m.p. 170°–171° C.

EXAMPLE 4

1,2-Bis [(3-ethylthiocarbonyl) thioureido] benzene (Compound 13)

8.7 g. (0.07 mol.) of S-ethyl chlorothiol formate were added to 7.8 g. (0.08 mol.) of potassium thiocyanate in 60 ml. of dioxane at room temperature under agitation, and mixture was heated and kept at a temperature of 35°–40° C. for 30 minutes. 3.3 g. (0.03 mol.) of o-phenylenediamine were dropped into the mixture while it was kept at a temperature of 10°–20° C. The resulting reaction mixture was kept at room temperature for 1 hour under agitation. Then dioxane was distilled off from the mixture and about 200 ml. of water were added to the residue.

8 g. of the resulting light yellow crystals were recrystallized from dioxane to obtain colorless prisms having decomposition point of 191°–192° C.

EXAMPLE 5

1,2-Bis [(3-benzyloxycarbonyl) thioureido] benzene (Compound No. 10)

25 g. (0.15 mol.) of chloroformic benzylester were added to 15 g. (0.15 mol.) of potassium thiocyanate in 70 ml. of acetone below a temperature of 10° C. with stirring, and the mixture was heated and kept at a temperature of 140° C. for 1 hour.

8.5 g. (0.075 mol.) of o-phenylenediamine were dropped into the mixture containing the resulting benzyloxycarbonylisothiocyanate by keeping a temperature below 10° C. with stirring.

The reaction mixture was heated on a steam bath for two hours under reflux, then it was cooled and 200 ml. of water was added to it.

The reaction mixture was extracted with 150 ml. of chloroform and the extract chloroform was washed with water and chloroform layer was dried with calcium chloride, then said chloroform was distilled off and the resulting residual material was dissolved in hot ethanol. After cooling ethanol solution, crystals separated and were filtrated.

White dust having a melting point of 171°–172° C. were obtained by recrystallization from ethanol.

EXAMPLE 6

1,2-Bis [3-(2-chloroethoxycarbonyl)-2-thioureido] benzene (Compound No 12)

28.0 g. (0.2 mol.) of chloroformic 2-chloroethylester were added to 19.5 g. (0.2 mol.) of potassium thiocyanate in 100 ml. of acetone at room temperature with stirring and the mixture was heated and kept at 40° C. on a water bath for 1 hour. 10.8 g. (0.1 mol.) of o-phenylenediamine were dropped into the mixture containing the obtained 2-chloroethoxycarbonylisothiocyanate at a temperature of 10°–20° C. on an ice water bath.

The reaction mixture was heated on a steam bath at a temperature of 30°–35° C. for 1 hour with stirring.

Then, the reaction mixture was cooled and filtrated, and obtained crystals were washed with water and methanol, and dried.

27 g. of crystals were obtained. Slight yellow plates having a decomposition point of 181°–182° C. were obtained by recrystallization from the mixture of dioxane and methanol.

EXAMPLE 7

1,2-Bis (3-allyloxycarbonyl-2-thioureido) benzene (Compound No. 15)

12 g. (0.1 mol.) of chloroform allylester were added to 10 g. (0.1 mol.) of potassium thiocyanate in 50 ml. of acetone at room temperture with stirring, and the mixture was heated and kept at a temperature of 40°–50° C. for 1 hour on a water bath.

4.3 g. (0.004 mol.) of o-phenylenediamine were dropped into the mixture containing the obtained alyloxycarbonylisothiocyanate at a room temperature.

The reaction mixture was heated on a steam bath for one hour under reflux. Then, the reaction mixture was cooled and cold water was added to it.

The separated crystals were filtrated and the obtained crystals were washed with water and methanol, and dried.

Colorless plates having a melting point of 166°–167° C. were obtained by recrystallization from methanol.

EXAMPLE 8

1,2-Bis [3-(2-propynyloxycarbonyl)-2-thioureido] benzene (Compound No. 16)

14.0 g. (0.118 mol.) of chloroformic 2-propynylester were added to 12.0 g. (0.123 mol.) of potassim thiocyanate in 70 ml. of acetone at room temperature with stirring, and the mixture was heated and kept at 40° C. on a water bath for 1 hour.

6.4 g. of o-phenylenediamine were dropped into the mixture containing the obtained 2-propynyloxycarbonylisothiocyanate at a temperature of 10°–20° C. on an ice water bath.

The reaction mixture was stirred for 1 hour, further heated at 40° C. for 30 minutes and allowed to stand for overnight at a room temperature, and water was added to the mixture.

Then, the separated crystals were filtrated and washed with water and methanol.

Slight yellow plates having a decomposition point of 172°–173° C. were obtained by recrystallization from methanol.

EXAMPLE 9

1,2-Bis [3-(4-chlorophenoxycarbonyl)-2-thioureido] benzene (Compound No. 17 )

17.2 g. of chloroformic 4-chlorophenylester were added to 9.3 l g. of potassium thiocyanate in 30 ml. of acetone at room temperature with stirring, and the mixture was heated and kept at a temperature of 40°–50° C. on a water bath for 1 hour.

3.3 g. of o-phenylenediamine were dropped into the mixture containing the resulting 4-chlorophenoxycarbonylisothiocyanate at a temperature of 0°–20° C.

The reaction mixture was heated and kept at a temperature of 40°–45° C. for 30 minutes.

Then, the reaction mixture was cooled and the precipitated crystals were filtrated, the obtained crystals were washed with water and methanol. White dust having a dcomposition point of 193° C. were obtained by recrystallization from acetone.

EXAMPLE 10

1,2-Bis [3-(4-methylphenoxycarbonyl)-2-thioureido]-4-chlorobenzene (Compound No. 18)

5.1 g. of chloroformic 4-methylphenylester were added to 3.13 g. of potassium thiocyanate in 15 ml. of acetone keeping temperature below 10° C. with stirring, and the mixture was heated and kept at a temperature of 32°–40° C. for 30 minutes. 1.4 g. of 4-chloro-O-phenylenediamine were dropped into the mixture containing the obtained 4-methylphenoxycarbonylisothiocyanate by keeping the temperature between 5° and 15° C.

The reaction mixture was heated and kept the temperature at 50° C. for 30 minutes. Then, the mixture was cooled and cold water added to it. The precipiated crystals were filtrated and the obtained crystals were washed with water and methanol.

The colorless crystals having a decomposition point of 191° to 192° C were obtained by recrystallization from acetone.

EXAMPLE 11

1,2-Bis [3-(4-chlorophenoxycarbonyl)-2thioureido]-4-methylbenzene (Compound No. 19)

11.5 g. of chloroformic 4-chlorophenylester were added to 6.3 g. of potassium thiocyanate in 30 ml. of acetone keeping the temperature below 10° C. with stirring, and the mixture was heated and kept the temperature between 30° and 40° C. for 1 hour.

2.4 g. of 4-methyl-O-phenylenediamine were dropped into the mixture containing the obtained 4-chlorophenoxycarbonylisothiocyanate by keeping the temperature at 5°–15° C.

The reaction mixture was heated and kept at the temperature of 50° C. for 1 hour. Then, the mixture was cooled and cold water added to it. The precipitated crystals were filtrated and the obtained crystals were washed with water and methanol.

The colorless crystals having a decomposition point of 199°–200° C. were obtained by recrystallization from dioxane.

EXAMPLE 12

1,2-Bis [3-(2-naphthoxycarbonyl)-2-thioureido] benzene (Compound No. 20)

19.2 g. of chloroformic 2-naphthylester were added to 9.7 g. of potassium thiocyanate in 50 ml. of acetone keeping the temperature below 10° C. with stirring, and the mixture was heated and kept at the temperature between 40° and 50° C. for 1 hour.

3.3 g. of O-phenylenediamine were dropped into the mixture containing the obtained 2-naphthoxycarbonylisothiocyanate by keeping the temperature between 5° and 15° C.

The reaction mixture was heated on a steam bath for 30 minutes under reflux, then it was cooled and cold water was added to it.

The precipitated crystals were filtrated and the obtained crystals were washed with water and methanol.

The yellow dust having a decomposition point of 191°–192° C. were obtained by recrystallization from dioxane.

EXAMPLE 13

1,2-Bis [3-(2-naphthoxycarbonyl)-2-thioureido]-4-nitrobenzene (Compound 21)

9.6 g. of chloroformic 2-naphthylester were added to 4.8 g. of potassium thiocyanate in 25 ml. of acetone keeping the temperature below 10° C. with stirring, and the mixture was heated and kept at a temperature of 40°–50° C. for 1 hour.

2.35 g. of 4-nitro-O-phenylenediamine dissolved in 15 ml. of acetone were dropped into the mixture containing the obtained 2-napthoxycarbonylisothiocyanate by keeping the temperature between 0° and 5° C.

The mixture was stirred at a room temperature for 3 hours, then it was cooled and filtrated. The obtained crystals were washed with methanol and water, further dried.

The yellow dust having a decomposition point of 180° C. were obtained by recrystallization from dioxane.

Some typical compounds of the present invention are listed in Table 1, along with some of their properties.

These typical compounds in Table 1 include merely some of the compounds of the present invention, so that the scope of the present invention is not intended to be limited only to those compounds listed in Table 1.

Table 1

| No. of Compd. | Structural Formula | Appearance | Melting Point or Decomposition Point(d) (°C) | Molecular Formula | C(%) | H(%) | N(%) |
|---|---|---|---|---|---|---|---|
| 1 | [structure: phenyl with NH-C(=S)-NH-C(=O)-O-CH₃ and NH-C(=O)-NH-C(=S)-O-CH₃ ortho substituents] | colorless prisms | 181.5–182.5(d) | $C_{12}H_{14}N_4O_4S_2$ | 42.35 (42.10) | 4.46 (4.09) | 16.70 (16.35) |
| 2 | [structure with -O-C₂H₅ groups] | colorless plates | 191(d) | $C_{14}H_{18}N_4O_4S_2$ | 45.35 (45.41) | 5.08 (4.85) | 14.90 (15.19) |
| 3 | [structure with -O-CH(CH₃)₂ groups] | colorless powder | 205–206(d) | $C_{16}H_{22}N_4O_4S_2$ | 48.40 (48.24) | 5.72 (5.53) | 13.87 (14.07) |
| 4 | [structure with -O-CH₂CH(CH₃)₂ groups] | pale yellow tablets | 197–198(d) | $C_{18}H_{26}N_4O_4S_2$ | 50.70 (50.70) | 6.35 (6.10) | 13.35 (13.15) |
| 5 | [4-methyl phenyl structure with -O-C₂H₅ groups] | pale yellow powder | 175–176(d) | $C_{15}H_{20}N_4O_4S_2$ | 46.70 (46.88) | 5.32 (5.22) | 14.30 (14.58) |
| 6 | [4-chloro phenyl structure with -O-C₂H₅ groups] | pale yellow powder | 170.5–171.5(d) | $C_{14}H_{17}ClN_4O_4S_2$ | 41.70 (41.53) | 4.57 (4.20) | 13.75 (13.84) |

Table 1-continued

| No. of Compd. | Structural Formula | Appearance | Melting Point or Decomposition Point(d) (° C) | Molecular Formula | Analysis For C(%) | H(%) | N(%) |
|---|---|---|---|---|---|---|---|
| 7 | NO$_2$-C$_6$H$_3$(NH-C(=S)-NH-C(=O)-O-C$_2$H$_5$) | light yellow plates | 205–205.5(d) | C$_{10}$H$_{17}$N$_5$O$_6$S$_2$ | 40.20 (40.48) | 4.16 (4.10) | 16.70 (16.87) |
| 8 | Cl$_2$-C$_6$H$_2$(NH-C(=S)-NH-C(=O)-O-C$_2$H$_5$) | light brown scales | 206–207(d) | C$_{14}$H$_{16}$Cl$_2$N$_4$O$_6$S$_2$ | 38.31 (38.27) | 3.71 (3.67) | 12.68 (12.75) |
| 9 | Cl$_3$-C$_6$H(NH-C(=S)-NH-C(=O)-O-C$_2$H$_5$) | pale brown powder | 180–181 | C$_{14}$H$_{15}$Cl$_3$N$_4$O$_6$S$_2$ | 35.53 (35.49) | 3.11 (3.19) | 11.91 (11.83) |
| 10 | C$_6$H$_4$(NH-C(=S)-NH-C(=O)-O-CH$_2$-C$_6$H$_5$)$_2$ | colorless prisms | 171–172 | C$_{24}$H$_{22}$N$_4$O$_4$S$_2$ | 58.45 (58.30) | 4.50 (4.45) | 11.40 (11.33) |
| 11 | C$_6$H$_4$(NH-C(=S)-NH-C(=O)-O-CH$_2$CH$_2$OCH$_3$)$_2$ | colorless needles | 170.5–171.5 | C$_{16}$H$_{22}$N$_4$O$_6$S$_2$ | 44.58 (44.70) | 5.23 (5.12) | 12.90 (13.02) |
| 12 | C$_6$H$_4$(NH-C(=S)-NH-C(=O)-O-C$_2$H$_4$Cl)$_2$ | colorless plates | 181–182(d) | C$_{14}$H$_{16}$Cl$_2$N$_4$O$_6$S$_2$ | 38.40 (38.25) | 3.45 (3.64) | 12.63 (12.75) |

Table 1-continued
| No. of Compd. | Structural Formula | Appearance | Melting Point or Decomposition Point(d) (°C) | Molecular Formula | Analysis For C(%) | H(%) | N(%) |
|---|---|---|---|---|---|---|---|
| 13 |  | colorless prisms | 191–192(d) | $C_{14}H_{18}N_4O_2S_4$ | 41.68 (41.80) | 4.38 (4.48) | 13.80 (13.94) |
| 14 |  | colorless needles | 122–123.5(d) | $C_{34}H_{58}N_4O_2S_4$ | 59.50 (59.82) | 8.43 (8.50) | 8.02 (8.21) |
| 15 |  | colorless leaflets | 166–167 | $C_{16}H_{18}N_4O_4S_2$ | 48.82 (48.77) | 4.59 (4.61) | 14.29 (14.22) |
| 16 |  | light brown plates | 172–173(d) | $C_{16}H_{14}N_4O_4S_2$ | 49.36 (49.27) | 3.58 (3.62) | 14.42 (14.37) |
| 17 | 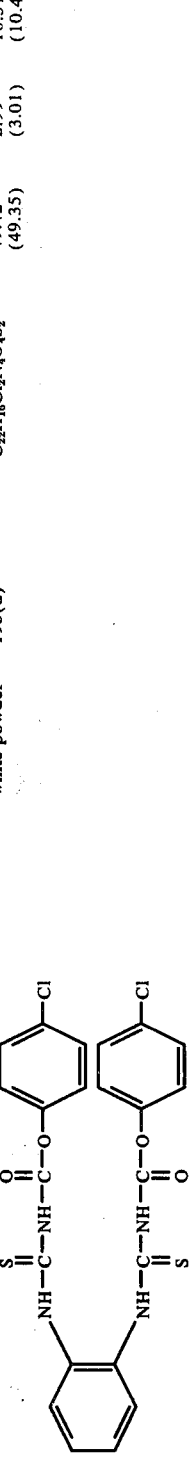 | white powder | 193(d) | $C_{22}H_{16}Cl_2N_4O_4S_2$ | 49.42 (49.35) | 2.99 (3.01) | 10.51 (10.46) |

Table 1-continued

| No. of Compd. | Structural Formula | Appearance | Melting Point or Decomposition Point(d) (°C) | Molecular Formula | C(%) | Analysis For H(%) | N(%) |
|---|---|---|---|---|---|---|---|
| 18 | (structure) | colorless crystals | 191–192(d) | $C_{24}H_{21}ClN_4O_4S_2$ | 54.51 (54.48) | 3.92 (4.00) | 10.60 (10.59) |
| 19 | (structure) | colorless crystal | 199–200(d) | $C_{23}H_{18}Cl_2N_4O_4S_2$ | 50.41 (50.27) | 3.19 (3.30) | 10.35 (10.20) |
| 20 | (structure) | yellow powder | 191–192(d) | $C_{30}H_{22}N_4O_4S_2$ | 63.60 (63.59) | 4.05 (3.91) | 10.06 (9.89) |
| 21 | (structure) | yellow powder | 180(d) | $C_{30}H_{21}N_5O_6S_2$ | 59.03 (58.91) | 3.51 (3.46) | 11.39 (11.45) |
| 22 | (structure) | colorless plates | 177–178(d) | $C_{13}H_{16}N_4O_6S_2$ | 43.65 (43.81) | 4.61 (4.52) | 15.58 (15.72) |

The compounds listed in Table 1 possess very superior fungicidal activity compared to known compounds.

In this invention usually a small but effective amount of te compounds is applied to plant surface by spraying, drenching or dusting to protect or control the microbes and diseases. The concentrations of the active ingredients in the fungicidal compositions of this invention vary according to type of formulation, and they are, for example, used in a range of 10–80 weight %, preferably 20–αweight %, in wettable powder, 10–70 weight percent, preferably 10–50 weight %, in emulsifiable concentrates, and 0.5–10 weight %, preferably 1–5 weight % in dust formulations. In the above formulation of the composition, auxiliary agents or materials, for example, inert mineral powders such as clay, talc and diatomaceous earth, dispersing agents such as sodium lignin sulfonate and casein, and wetting agents such as alkylarylsulfonate and polyoxyethylene alkylphenol, may be employed according to type of the formulation for combatting fungi and bacteria. Furthermore, the composition may be applied as a mixture with other fungicides, insecticides, acaricides, plant growth regulators and fertilizers.

The non-limiting examples for the fungicidal compositions are illustrated as follows:

EXAMPLE 14

| Wettable Powder | Parts by Weight |
|---|---|
| Compound 2 | 30 |
| Sodium alkylsulfonate | 5 |
| Diatomaceous earth | 65 |

These were mixed and micronized in jet pulverizer to a particle size of 10–20 microns. In practical use, the micronized mixture is diluted to a concentration of 0.01 to 0.05% of active ingredient with water. The suspension is applied as spray or drench.

EXAMPLE 15

| Emulsifiable Concentrate | Parts by Weight |
|---|---|
| Compound 2 | 10 |
| Xylene | 45 |
| Cyclohexanone | 39 |
| Phenyl polyoxyethylene | 6 |

These can be mixed to obtain a solution. In practical use, the solution is diluted with water to a concentration of 0.01 to 0.05% of active ingredient and this suspension is sprayed or used for drenching.

EXAMPLE 16

| Dust Formulation | Parts by Weight |
|---|---|
| Compound 5 | 2 |
| Talc | 98 |

These can be mixed and crushed to a fine powder. The dust formulation is usually applied as dusting powder at a rate of 3 to 5 kg. per 10 are.

In the Examples 14–16, it is not intended to limit the emulsifying, wetting or dispersing agents, carriers and solvents to the ones described by way of illustration.

With regard to mammalian toxicity of the typical compound, for example, that of compound 2 in Table 1 is 15,000 mg./kg. and that of compound 1 is up to 3,000 mg./kg. as the value of acute order LD 50 for mice.

The superior fungicidal effects of the novel compounds of this invention are clearly illustrated by the following tests.

TEST 1

Test For Control Of Rice Blast Disease

The compound to be tested was applied as water-diluted solution of wettable powder prepared according to the method of Example 14. The potted rice plants grown to a 3 leaf stage were sprayed at a rate of 25 cc./pot with solutions of the test materials. One day later, the plants were inoculated with a spore suspension of rice blast fungus, Piricularia oryzae, and held under the condition of incubation (at about 100% relative humidity and 26% C.) in a wet cabinet for 24 hours. Then the plants were moved to a greenhouse bench. Ten days after incubation, number of lesions per pot were examined and evaluation of percent disease control was based upon the percentage of lesions occurring on the untreated check. The results are shown in Table 2.

Table 2

| Compd. No. | Conc. of Active Ingredient (γ/ml) | Avg. No. of Lesion per Pot | Control Value (%) | Phytotoxicity |
|---|---|---|---|---|
| 2 | 500 | 2.5 | 97.5 | none |
| 5 | 300 | 1.0 | 99 | " |
| 9 | 500 | 0.0 | 100 | " |
| 11 | " | 12.5 | 87.4 | " |
| 12 | " | 3.0 | 97 | " |
| 13 | " | 16.0 | 83.8 | " |
| 14 | " | 1.0 | 99 | " |
| 15 | " | 4.0 | 96 | " |
| 16 | " | 0.5 | 99.5 | " |
| Pentachlorobenzyl alcohol | " | 4.0 | 96.0 | " |
| check | — | 99.5 | 0 | — |

TEST 2

Test for Control of Cucumber Anthracnose

The potted cucumber plants grown to a three leaf stage were sprayed at a rate of 50 ml. per 3 plants with water-diluted solution of the wettable powder prepared by the method of Example 14. One day later, the plants were inoculated with a spore suspension of cucumber anthracnose fungus, Colletotrichum lagenarium, and held under the condition of incubation (at about 100% relative humidity and 26° C.) in a wet cabinet for 20 hours. Then the plants were moved to a greenhouse bench. Seven days after incubation, average number of lesions per leaf were counted and evaluation of percent disease control was based upon the percentage of lesions occurring on the untreated check. The results are shown in Table 3.

Table 3

| Compd. No. | Conc. of Active Ingredient (γ/ml) | Avg. No. of Lesion per Pot | Control Value (%) | Phytotoxicity |
|---|---|---|---|---|
| 1 | 300 | 8.2 | 97.3 | none |
| 2 | " | 0.0 | 100 | " |
| 3 | " | 10.5 | 96.7 | " |

TEST 3.

Field Test for Control of Cercospora Leaf Spot of Sugar Beets

This test was conducted in an attempt to determine the effect of inhibition in development of the Cerospora leaf spot on leaves of sugar beets by the foliage spraying. The field was arranged in a randomized-block design with 4 replicate plots of each treatment consisted of 25 m² per plot. The diluted sprays were applied at the rate of 100 liters per 10 are as a single application after incipient infection was apparent in the leaves. One month after spraying, disease data were taken by counting the infected leaves on 50–60 sugar beets selected at random from each plot and leaf spot severity was rated on a scale ranging from 0 to 5 in which 0 = no leaf spot and 5 = most of the leaves dead from disease. The results are shown in Table 4.

Table 4

| Compositions | Dilution Ratio W/Water For Spray | Disease Rating At the time of Spraying | Disease Rating One Month After Spraying |
|---|---|---|---|
| Wettable powder containing 25% of Compound 2 | 1 to 250 | 0.65 | 0.97 |
| TPTA* wettable powder (20% active) | 1 to 1,000 | 0.77 | 2.71 |
| Check | — | 0.70 | 4.61 |

TPTA* = Triphenyltin acetate

TEST 4

Test for Control of Rice Sheath Blight Disease

The compounds to be tested were applied as water-diluted solution of wettable powder prepared by the method of Example 14. The potted rice plants (24–25 plants per single pot) grown to a 5 leaf stage were sprayed at a rate of a 25 cc./pot with solution of the test material. Two days later, the plants were inoculated with mycelia of the rice sheath blight fungus, *Corticium sasaki*, grown in a culture medium. The plants were transferred to a wet cabinet and held under the condition of incubation (at 100% relative humidity and 25°–30° C.) for 2 days. At the end of this time, the plants were moved to a greenhouse bench. Eight days after incubation, number of plants infected were examined in each test pot and the data were recorded as infection rating made on a scale of 0 = no infected; 1 = up to 5 plants infected/pot; 2 = 6–15 plants infected/pot; 3 = 16 or more plants infected/pot. The results are shown in Table 5.

Table 5

| Compd. No. | Conc. of Active Ingredient (γ/ml) | Infection Rating | Phytotoxicity |
|---|---|---|---|
| 1 | 500 | 0.00 | none |
| 2 | " | 0.00 | " |
| 3 | " | 0.00 | " |
| 5 | " | 0.30 | " |
| 6 | " | 0.30 | " |
| 10 | " | 0.50 | " |

We claim:

1. A fungicidal composition comprising an inert carrier and a fungicidally effective amount of at least one compound of the formula:

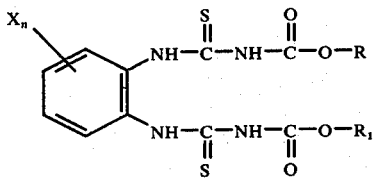

wherein each of R and $R_1$ represents a member of the group consisting of alkyl containing from 1 to 12 carbon atoms, alkyl containing from 1 to 2 carbon atoms substituted with halogen or methoxy, alkenyl containing 2 to 3 carbon atoms, alkynyl containing 2 to 3 carbon atoms, benzyl, naphthyl, phenyl and phenyl substituted with halogen or methyl; each X represents halogen, nitro or methyl; n represents an integer from 0 to 3.

2. A composition according to claim 1 in which n equals zero, and each of R and $R_1$ is alkyl containing 1 to 12 carbon atoms.

3. A composition according to claim 1 in which n equals zero, and each of R and $R_1$ is alkyl containing 1 to 2 carbons atoms substituted with halogen or methoxy.

4. A composition according to claim 1 in which n equals zero, and each of R and $R_1$ is benzyl, naphthyl, phenyl and phenyl substituted with halogen or methyl.

5. A composition according to claim 2 in which each of R and $R_1$ is methyl.

6. A composition according to claim 2 in which each of R and $R_1$ is ethyl.

7. A composition according to claim 2 in which each of R and $R_1$ is isopropyl.

8. A fungicidal composition comprising an inert carrier and a fungicidally effective amount of at least one compound selected from the group consisting of 1,2 - bis [(3-methoxycarbonyl) thioureido] benzene 1,2 - bis [(3-ethoxycarbonyl) thioureido] benzene 1,2 - bis [(3-isopropoxycarbonyl) thioureido ] benzene 1,2 - bis [(3- isobutoxycarbonyl) thioureido ] benzene 3,4 - bis [(3-ethoxycarbonyl) thioureido ] toluene 1,2 -bis [(3-ethoxycarbonyl) thioureido]-4-chlorobenzene 1,2 - bis [(3-ethoxycarbonyl) thioureido]-4-nitrobenzene 1,2 - bis [(3-ethoxycarbonyl) thioureido]-4,5-dichlorobenzene 1,2 - bis [(3-ethoxycarbonyl) thioureido ]-3,4,6-trichlorobenzene 1,2 - bis [(3-benzyloxycarbonyl) thioureido] benzene 1,2 - bis [(3-betamethoxyethoxycarbonyl) thioureido ] benzene 1,2 - bis [3-(2-chloroethoxycarbonyl) thioureido] benzene
1,2 - bis [(3-ethylthiocarbonyl) thioureido] benzene
1,2 - bis [(3-dodecylthiocarbonyl) thioureido ] benzene
1,2 - bis [(3-allyloxycarbonyl) thioureido] benzene
1,2 - bis [3-(2-propynyloxycarbonyl) thioureido] benzene
1,2 - bis [3-(4-chlorophenoxycarbonyl) thioureido] benzene
1,2 - bis [3-(4-methylphenoxycarbonyl) thioureiod ]-4-chlorobenzene
1,2 - bis [3-(4-chlorophenoxycarbonyl) thioureido]-4-methylbenzene
1,2 - bis [3 -(2-naphthoxycarbonyl) thioureido ) benzene
1,2 - bis [3-(2-naphthoxycarbonyl) thioureido]-4-nitrobenzene and
1 - (3-ethoxycarbonyl-2-thioureido)-2-(3-methoxycarbonyl-2-thioureido) benzene.

9. A method of preventing injury due to fungi comprising applying to the locus to be protected an effective amount of at least one compound of the formula:

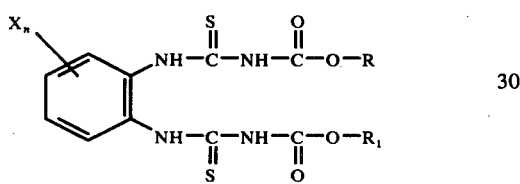

wherein each of R and R₁ represents a member of the group consisting of alkyl containing from 1 to 12 carbon atoms, alkyl containing from 1 to 2 carbon atoms substituted with halogen or methoxy, alkenyl containing 2 to 3 carbon atoms, alkynyl containing 2 to 3 carbon atoms, benzyl, naphthyl, phenyl and phenyl substituted with halogen, or methyl; each X represents halogen, nitro or methyl; n represents an integer from 0 to 3.

10. The method according to claim 9 in which n equals zero, and each of R and R₁ is alkyl containing 1 to 12 carbon atoms.

11. The method according to claim 9 in which n equals zero, and each of R and R₁ is alkyl containing 1 to 2 carbon atoms substituted with halogen or methoxy.

12. The method according to claim 9 in which n equals zero, and each of R and R₁ is benzyl, naphthyl, phenyl and phenyl substituted with halogen or methyl.

13. The method according to claim 10 in which each of R and R₁ is methyl.

14. The method according to claim 10 in which each of R and R₁ is ethyl.

15. The method according to claim 10 in which each of R and R₁ is isopropyl.

16. A method for preventing injury due to fungi comprising applying to the locus to be protected an effective amount of at least one compound selected from the group consisting of
1,2 - bis [(3-methoxycarbonyl) thioureido] benzene
1,2 - bis [(3-ethoxycarbonyl) thioureido] benzene
1,2 - bis [(3-isopropoxycarbonyl) thioureido] benzene
1,2 - bis [(3-isobutoxycarbonyl) thioureido] benzene
3,4 - bis [(3-ethoxycarbonyl) thioureido] toluene
1,2 - bis [(3-ethoxycarbonyl) thioureido]-4-chlorobenzene
1,2 - bis [(3-ethoxycarbonyl) thioureido]-4-nitrobenzene
1,2- bis [(3-ethoxycarbonyl) thioureido]-4,5-dichlorobenzene
1,2 - bis [(3-ethoxycarbonyl) thioureido]-3,4,6-trichlorobenzene
1,2 - bis [(3-benzyloxycarbonyl) thioureido] benzene
1,2 - bis [(3-betamethoxyethoxycarbonyl) thioureido ] benzene
1,2 - bis [3-(2-chloroethoxycarbonyl) thioureido ] benzene
1,2 - bis [(3-ethylthiocarbonyl) thioureido] benzene
1,2 - bis [(3 -dodecylthiocarbonyl) thioureido] benzene
1,2 - bis [(3-allyloxycarbonyl) thioureido ]benzene
1,2 - bis [(3-(2-propynyloxycarbonyl) thioureido ] benzene
1,2 - bis [3-(4-chlorophenoxycarbonyl) thioureido] benzene
1,2 - bis [3-(4-methylphenoxycarbonyl) thioureido]-4-chlorobenzene
1,2 - bis [3-(4-chlorophenoxycarbonyl) thioureido]-4-methylbenzene
1,2 -bis [3-(2-naphthoxycarbonyl) thioureido] benzene
1,2 - bis [3-(2-naphthoxycarbonyl) . thioureido]-4-nitrobenzene and
1 - (3-ethoxycarbonyl-2-thioureido)-2-(3-methoxycarbonyl-2-thioureido) benzene.

* * * * *

UNITED STATES PATENT AND TRADEMARK OFFICE
CERTIFICATE OF CORRECTION

PATENT NO. : 4,029,813
DATED : June 14, 1977
INVENTOR(S) : Teruhisa Noguchi et al It is certified that error appears in the above-identified patent and that said Letters Patent are hereby corrected as shown below:

Column No. 2, Lines 1 and 2
Delete "and by washing with water" (second appearance)

Column No. 3, Line 51
"140°C" should read -- 40°C --.

Column No. 5, Line 7
"9.3 1 g" should read -- 9.3 g --.

Column No. 15, Line 5
"te" should read -- the --.

Column No. 15, Line 11
"20-α" should read -- 20-60 --.

Column No. 16, Line 25
"26%" should read -- 26° --.

Column No. 16, Table 2
The word "alcohol" should be deleted from the second column and placed under the word "benzyl" in the column entitled "Compd. No.".

Column No. 18, Line 36
"carbons" should read -- carbon --.

Signed and Sealed this

Twentieth Day of September 1977

[SEAL]

Attest:

RUTH C. MASON
Attesting Officer

LUTRELLE F. PARKER
Acting Commissioner of Patents and Trademarks